(12) United States Patent
Campo et al.

(10) Patent No.: US 9,254,933 B2
(45) Date of Patent: Feb. 9, 2016

(54) METHOD OF INERTING ASEPTIC TANKS

(75) Inventors: Philippe Campo, Montigny le Bretonneux (FR); Fabrice Bouquin, Guyancourt (FR)

(73) Assignee: L'Air Liquide Société Anonyme Pour L'Étude Et L'Exploitation Des Procedes Georges Claude, Paris (FR)

( * ) Notice: Subject to any disclaimer, the term of this patent is extended or adjusted under 35 U.S.C. 154(b) by 360 days.

(21) Appl. No.: 13/581,151

(22) PCT Filed: Jan. 27, 2011

(86) PCT No.: PCT/FR2011/050158
§ 371 (c)(1),
(2), (4) Date: Aug. 24, 2012

(87) PCT Pub. No.: WO2011/104452
PCT Pub. Date: Sep. 1, 2011

(65) Prior Publication Data
US 2013/0202478 A1  Aug. 8, 2013

(30) Foreign Application Priority Data
Feb. 25, 2010  (FR) ...................................... 10 51343

(51) Int. Cl.
| | | |
|---|---|---|
| *A61L 2/18* | (2006.01) | |
| *B65B 31/04* | (2006.01) | |
| *A23L 3/00* | (2006.01) | |
| *B08B 9/08* | (2006.01) | |
| *A61L 2/20* | (2006.01) | |

(52) U.S. Cl.
CPC . *B65B 31/04* (2013.01); *A23L 3/00* (2013.01); *A61L 2/18* (2013.01); *A61L 2/20* (2013.01); *B08B 9/08* (2013.01); *A61L 2202/17* (2013.01); *A61L 2202/182* (2013.01); *A61L 2202/23* (2013.01)

(58) Field of Classification Search
CPC ................. A61L 2/16; A61L 2/18; A61L 2/20
USPC .............................. 422/3, 26, 28; 99/467, 468
See application file for complete search history.

(56) References Cited

U.S. PATENT DOCUMENTS

| | | | |
|---|---|---|---|
| 4,325,296 A * | 4/1982 | Ukai et al. ...................... | 99/468 |
| 5,544,669 A | 8/1996 | Manabe et al. | |
| 6,030,580 A * | 2/2000 | Raasch et al. ................... | 422/40 |
| 2005/0276721 A1* | 12/2005 | Centanni ......................... | 422/28 |

FOREIGN PATENT DOCUMENTS

| | | |
|---|---|---|
| WO | WO 99/23016 | 5/1999 |
| WO | WO 03/070024 | 8/2003 |

OTHER PUBLICATIONS

International Search Report for PCT/FR2011/050158, mailed May 31, 2011.

* cited by examiner

*Primary Examiner* — Sean E Conley
*Assistant Examiner* — Donald Spamer
(74) *Attorney, Agent, or Firm* — Christopher J. Cronin

(57) ABSTRACT

The invention relates to a method for treating storage or product preparation tanks, tanks of the type which regularly undergo a hot aseptic washing step, followed by a cold water rinsing step, the method being characterized in that an inert gas is injected into the tank during all or part of the rinsing step.

15 Claims, 2 Drawing Sheets

METHOD OF INERTING ASEPTIC TANKS

CROSS-REFERENCE TO RELATED APPLICATIONS

This application is a § 371 of International PCT Application PCT/FR2011/050158, filed Jan. 27, 2011, which claims § 119(a) foreign priority to French patent application 1051343, filed Feb. 25, 2010.

BACKGROUND

1. Field of the Invention

The present invention relates to the area of methods for inerting tanks used for the storage or also for the preparation of products and is concerned particularly with tanks described as "aseptic".

2. Related Art

Document WO03/070024 illustrates this technical area.

More generally, in numerous industries, it is necessary to prepare or to hold products in storage in tanks or containers under controlled atmospheres with a low residual oxygen content. This requirement may result in variable stresses depending on the nature of the products in storage, and associated in particular with reasons of safety and with the desire to preserve the quality of the product, because of the susceptibility of the products in storage to oxidation, etc.

This holding of such stocks under an atmosphere with a low concentration of oxygen is commonly referred to as "inerting".

Inerting thus consists of replacing a volume of air present inside the tank to be inerted by a volume of a gas considered to be inert under the conditions of use in question. The gases that are used most frequently in such operations are nitrogen, argon or carbon dioxide, or mixtures thereof.

The techniques most commonly used to inert such tanks, and thus to replace air by inert gas, include:

Purging by a piston effect. This technique involves introducing the inert gas at a point opposite the outlet for the purged (evacuated) gas. This technique is used in particular for small cross sections, and very rarely for tanks, due to obvious constraints relating to the dispersion of the gas. The quantity of inert gas consumed is close to one volume of gas per volume of gas to be purged.

Inerting by dilution. This technique is widely used, and it is suitable for capacities of all sizes. It involves injecting the inert gas through an orifice and then proceeding with the successive dilution of the air that is present inside the tank. The said dilution is maintained until the desired concentration of residual oxygen is reached.

The quantity of inert gas consumed by this technique is close to 3 volumes of gas per volume of capacity to be inerted, in order to achieve a concentration of residual oxygen typically between 2 and 5%.

Inerting by compression and expansion. This technique is very rarely used to inert a tank. In fact, this technique requires either the pressure of the tank to be lowered in order to eliminate a proportion of the air that is present, or the pressure of the tank to be increased in order to facilitate the dilution. However, tanks are very rarely suitable for the required working pressures.

The quantity of inert gas consumed by this technique depends on the number of cycles used. It is often in the order of between 1 and 2 volumes of inert gas per volume of the tank.

Let us now consider the particular case of tanks described as "aseptic".

Certain industries, such as the agri-food or pharmaceutical industry (for obvious reasons that we will not explore in greater detail here), are obliged to undertake regular washing of their tanks in the context of the aseptisization of these tanks.

In the majority of cases, aseptic washing involves washing the tank with a hot alkaline solution at a temperature close to 80° C. This is followed immediately afterwards, and without waiting for the tank to cool down, by rinsing the tank with cold water. This cold water (10 to 25° C.) is injected through the same projection elements (of the washing balls type) that are situated at the top of the tank and were previously used to supply the hot washing solution.

It will be appreciated that this thermal cycling brings about a reduction in the pressure of the tank, which reduction in pressure sucks in external air.

More precisely, during the hot washing step, the atmosphere of the vessel is filled with a gaseous mixture comprising the gas that is initially present inside the vessel, this being either air or an inert gas if the tank had been inerted initially, and with water vapor, of which the percentage depends on the temperature (this can be appreciated more readily below from the curves).

Subsequent rinsing of the vessel with cold water causes the water vapor to condense, thereby bringing about a reduction in pressure if the tank is closed, or the aspiration of a gas, in this case air, if the vessel is open to the atmosphere.

In the case of tanks of which the atmosphere is controlled (inerted), this venting is often effected by opening a vent permitting the admission of air during the rinsing phase, the consequence of which is to cause the admission of a large volume of air, which it is necessary to eliminate at a later stage by one of the conventional inerting techniques already mentioned above.

The use of conventional inerting techniques require:
A significant down time for the vessel to bring the concentration of oxygen down to a sufficiently low value.
A significant consumption of gas.
Haphazard management of the inerting process without the excessive consumption of inert gas, except for controlling the atmosphere by analysis of the residual oxygen, which represents a costly solution, in particular in the case of a plurality of vessels requiring to be inerted.

SUMMARY OF THE INVENTION

It will be appreciated, against this overall background, in addition to being one of the objects of the present invention, that it would be advantageous to be able to have available a new method for inerting aseptic tanks, permitting a tank, after its aseptic washing step, to retain an atmosphere with a low residual oxygen level, at the same time making it possible to achieve:
an almost zero down time for the vessel
an optimized consumption of gas largely corresponding to the stoichiometry
preferentially, automatically assured management of the quality of the inerting.

As will be appreciated in more detail from the following, the method according to the invention proposes to perform a gaseous "flash" treatment of the tank during all or part of the rinsing step, and at a high rate of flow, with the help of an inert gas.

For this purpose, and in order better to explain the foregoing, according to one of the embodiments of such a gaseous treatment according to the invention:

A/ a predetermination is made of the quantity of inert gas required in order to perform this gaseous treatment, and it is possible to envisage different ways of making this predetermination according to the invention, for example the following procedure in particular:

a) after hot washing of the tank, and during its rinsing (thus during its traditional operation according to the prior art), the curve for the decrease in the temperature of the tank, which occurs during this rinsing step, is established, and a quantity of inert gas required in order to perform the flash treatment is deduced from this curve; this is illustrated below with very practical examples.

The curve for monitoring the temperature of the tank during rinsing in its traditional operation makes it possible to determine in particular:

i) the initial temperature before the start of rinsing;
    j) the period during which the requirement for gas is at its highest (this corresponds to the abrupt drop in temperature) and the associated temperature;
    k) the time taken to reach the final equilibrium temperature of the vessel (and the associated temperature).

b) it is also possible, however, to establish this requirement in a less precise and more approximate manner, based on experience, according to the principal indications of the washing temperature, the temperature of the rinsing water and the rinsing time that are typical of the user size in question, and then to adjust the injected flow more accurately at the time of the first installation tests.

c) finally, and still for illustrative purposes, this requirement for gas can be determined and the injected flow can be regulated according to a method that is proportional to the temperature of the vessel (this method is described in more detail later in the present application).

In this case, too, after the hot washing of the tank and during its rinsing step (thus during its traditional operation according to the prior art), the curve for the decrease in the temperature of the tank, which occurs during this rinsing step, will have been established.

This embodiment can be summarized by stating that consideration is also given to the water vapor pressure curve as a function of the temperature inside an enclosed space, and that a given volume of nitrogen (volume V in m$^3$) required to suppress the water vapor (as if the temperature of the vessel was 0° C.) will correspond to each temperature of the vessel.

B/ once this requirement for inert gas has been predetermined, by the use of one or other of these examples of methods, compensation for this requirement is made by injecting a very large flow of inert gas (this notion of a "large" flow is explained in more detail below), the said injection preferably commencing during the interim period between washing and rinsing, and it being possible for the injection to continue, or not, during all or part of the rinsing per se according to the temperature set point that it is wished to achieve.

By way of illustration, the injection commences a few seconds before opening the inlet valve for the cold rinsing water, and the flash injection is stopped once the temperature of the vessel has reached a given set point, for example 25° C., even if the step of rinsing the vessel with cold water is continuing at this point.

It is, in fact, recommended according to the invention for the gas to be injected preferably during the whole of the rinsing step, but otherwise essentially until the end of the period of the abrupt drop in temperature, which will be better appreciated in the context of examples provided below.

As outlined above, it is preferred according to the invention for the injection to commence before the start of the rinsing step (before opening the water inlet valve), although it is possible without inconvenience for this injection to commence a few seconds after the start of the rinsing step (for example between 1 and 10 seconds after), involving the intake of a small amount of air, which, depending on the result that it is wished to achieve in terms of residual oxygen, is not necessary detrimental.

It should be noted that a slight flow of inert gas can be maintained advantageously in certain cases, in particular for open tanks, in order to prevent pollution of the atmosphere by the intake of air.

In fact, when the flash injection is stopped, and even if the temperature does not drop any further, or hardly any further, the vessel may be left for several hours without being used. In this case, and in particular if the vessel is in permanent communication with the atmosphere via a large vent, an intake of air can occur over time, such an intake of air being all the more likely if the temperature continues to drop.

This intake of air can be avoided by maintaining a slight flow of gas, for example nitrogen (for example between 2 and 5 Nm$^3$/h), over an open vessel of this kind.

It should also be noted that such an intake of air can also take place if a product which would not be in equilibrium with the atmosphere (which is generally the case) is introduced into the vessel. In fact, the product would then "pump" a proportion of the gas from the atmosphere, all the more rapidly as the distance from the state of equilibrium increases, and even more so if it is agitated. The "pumped" atmosphere would involve an intake of air. Once again, maintaining a slight flow of inert gas provides a solution to this phenomenon.

As will be clearly apparent to a person skilled in the art, according to the prior art, during rinsing of the vessel with cold water, the water vapor will condense, resulting either in a reduction in pressure if the tank is closed, or in the aspiration of a gas, in this case air, when the vessel is open to the atmosphere. Thanks to the embodiment of the method according to the invention, however, it is an inert gas that is involved here, which changes everything.

The present invention thus relates to a method for treating tanks used for the storage and/or the preparation of products, these being tanks of the type which at more or less regular intervals (whenever this is necessary) undergo a hot aseptic washing step, followed by a cold water rinsing step, the method being characterized in that an inert gas is injected into the tank during all or part of the rinsing step.

It should be noted that document WO03/070024 referred to above in fact adopts an entirely different embodiment to that proposed here, since this document proposes to fill the tank completely with water and only then to inject the inert gas in order to expel the water from the tank (reference is made specifically to the foot of page 2 of the document and to FIGS. 2 and 3).

Notwithstanding the fact that this is an absurd solution in economic terms, because of the induced consumption of water and its pumping, it is also different from that which is claimed here, which proposes the injection of gas into the tank during all or part of the rinsing step, and thus during a rinsing water injection phase, in particular in order to benefit from the reduction in pressure generated by the cooling of the vessel and thus to optimize the consumption of gas.

According to one of the embodiments of the present invention, the flow of inert gas to be injected is determined by the following formula:

$$Q_1 = (V1_{gas}/t_1) \times 60$$

(in Nm$^3$/h of inert gas)

where:

$Q_1$=the flow of inert gas to be injected during the section of the curve corresponding to the most abrupt drop in temperature $V1_{gas}=(P_i-P_1)\times V_{vessel}$ $V_{vessel}$=the volume of the vessel of the tank in m$^3$ $P_i$=the water vapor saturation pressure at the temperature Ti of the vessel at the end of the washing step (in bar)

$P_1$=the water vapor saturation pressure at the temperature $T_1$ of the vessel at the end of the section of the curve corresponding to the most abrupt drop in temperature (in bar)

$t_1$=the duration of the section of the curve corresponding to the most abrupt drop in temperature.

According to another of the embodiments of the invention, two flows of inert gas to be injected $Q_1$ and $Q_2$ are determined and applied according to the following formulae:

$$Q_1=(V1_{gas}/t_1)\times 60$$

(in Nm$^3$/h of inert gas)

where:

$Q_1$=the flow of inert gas to be injected during the section of the curve corresponding to the most abrupt drop in temperature $V1_{gas}=(P_i-P_1)\times V_{vessel}$ $V_{vessel}$=the volume of the vessel of the tank in m$^3$ $P_i$=the water vapor saturation pressure at the temperature Ti of the vessel at the end of the washing step (in bar)

$P_1$=the water vapor saturation pressure at the temperature $T_1$ of the vessel at the end of the section of the curve corresponding to the most abrupt drop in temperature (in bar)

$t_1$=the duration of the section of the curve corresponding to the most abrupt drop in temperature.

and:

$$Q_2=(V2_{gas}/(t_f-t_1))\times 60$$

(in Nm$^3$/h of inert gas)

where:

$Q_2$=the flow of inert gas to be injected during the section of the curve corresponding to the slowest drop in temperature, the said section following the section of the curve exhibiting the most abrupt drop in temperature $V2_{gas}=(P_1-P_2)\times V_{vessel}$ $V_{vessel}$=the volume of the vessel in m$^3$ $P_1$=the water vapor saturation pressure at the temperature $T_1$ of the vessel at the end of the section of the curve corresponding to the most abrupt drop in temperature (in bar)

$P_2$=the water vapor saturation pressure at the temperature $T_f$ corresponding to the end of the section of the curve corresponding to the slowest drop in temperature (in bar)

$t_1$=the duration of the section of the curve corresponding to the most abrupt drop in temperature $t_f$=the time taken, from the start of the rinsing step, to achieve the final equilibrium temperature ($t_f-t_1$ thus corresponds to the duration of the slow descent phase of the temperature of the vessel until it reaches its state of equilibrium).

As better illustrated below, the experiments undertaken by the applicant clearly show the positive contribution of the invention.

BRIEF DESCRIPTION OF THE FIGURES

Other characteristics and advantages of the present invention will thus appear more clearly in the following description, which is given for illustrative purposes, although entirely without limitation, and is made with reference to the accompanying drawings, in which.

DETAILED DESCRIPTION OF THE INVENTION

Figure 1:
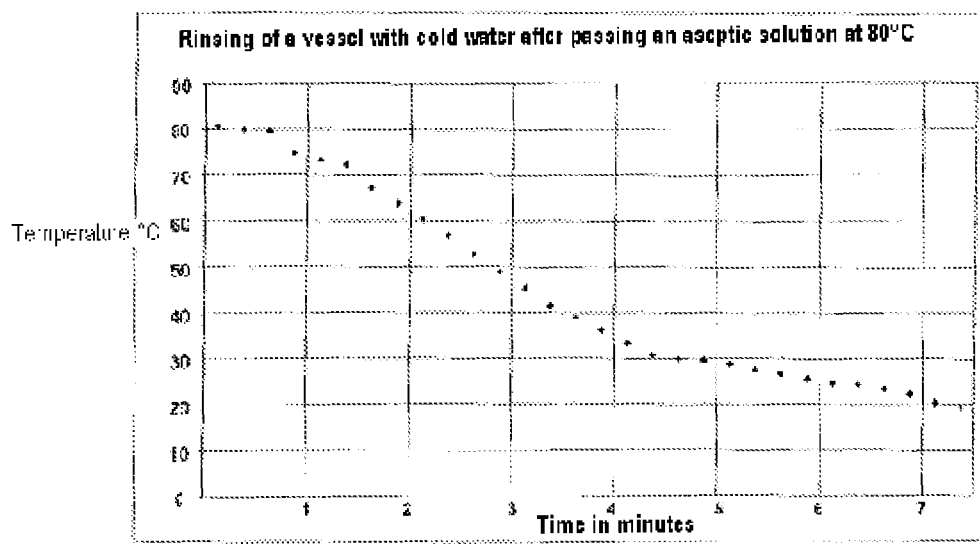
FIG. 1 illustrates an example of the determination of a temperature drop curve during rinsing of a vessel.

The temperature of a vessel at the moment of its rinsing and cooling (after passage of the washing solution at 80° C.) has thus been recorded, which recording is shown in FIG. 1. This vessel will be the one that is used for the examples, one of which is for comparative purposes and the other is according to the invention, and are reported below in the present description.

The presence of at least two time periods can be clearly distinguished on this cooling curve:

significant (abrupt) cooling and thus an associated equivalent reduction in pressure, gentle cooling (slower and of low amplitude) and an associated equivalent reduction in pressure.

On the other hand, the following data can be observed:

the initial temperature before the start of the rinsing step is Ti=80° C.

the period during which the drop in temperature is at its steepest, and thus during which the requirement for an inert gas is at its greatest, this period being close to $t_1$=4 min the temperature at the end of this first period (steep drop) is in the order of $T_1$=30° C.

the time taken to reach the final temperature is close to $t_f$=7 min the final temperature at this point is about $T_f$=20° C.

As already explained above in the present description, the requirement for inert gas in the course of this cooling corresponds to a great extent to the compensation of the difference in the partial water vapor pressure at the various temperatures.

Figure 2:
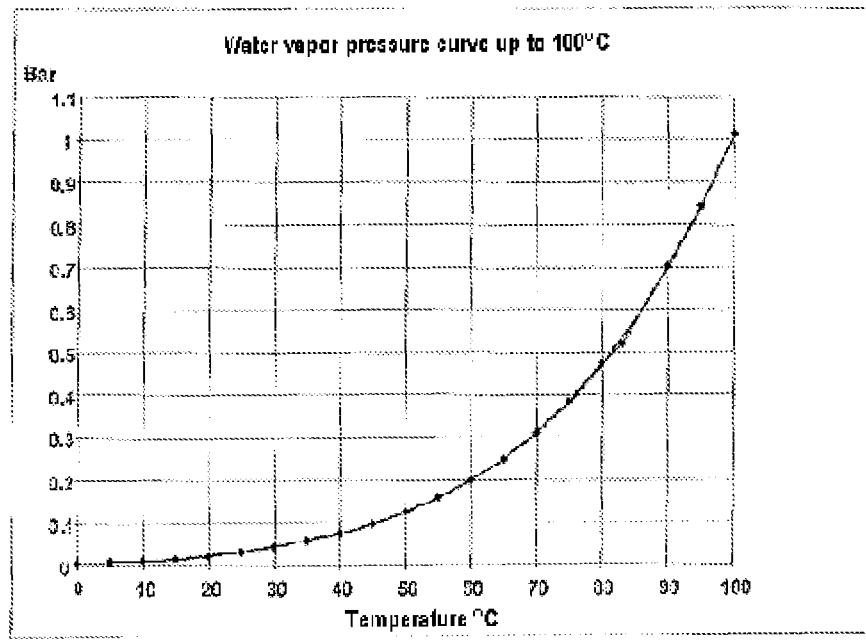
FIG. 2 depicts the partial pressure of the water as a function of the temperature inside a closed system.

Reference can be made to the graph attached hereto in FIG. 2 below, which represents the partial water pressure as a function of the temperature inside a closed system.

The following data can thus be derived in conjunction with the curve in FIG. 1:

the partial water pressure at the initial temperature Ti=80° C. is close to Pi=0.474 bar the partial water pressure at the temperature $T_1$=30° C. is close to $P_1$=0.042 bar the partial water pressure at the final temperature $T_f$=20° C. is close to $P_2$=0.023 bar.

The requirement for inert gas $V_{gas}$ thus corresponds to the volume of the vessel $V_{vessel}$ multiplied by the difference in the partial water vapor pressure between each step, as described in detail below.

For the step associated with a rapid drop in temperature, during the period $t_1$=4 min, the requirement is for:

$$V1_{gas}=(Pi=0.474\text{ bar}-P_1=0.042\text{ bar})\times V_{vessel}$$

For the step associated with a slow drop in temperature, permitting the final equilibrium temperature of the vessel to be reached at the time $t_f$=7 min, the requirement is for:

$$V2_{gas}=(P_1=0.042\text{ bar}-P_2=0.023\text{ bar})\times V_{vessel}$$

Thus, for a vessel having a volume $V_{vessel}$=75 m$^3$, the requirements at the different steps are:

$V1_{gas}=(0.474-0.042)\times 75=32.4$ m³ of gas and $V2_{gas}=(0.042-0.023)\times 75=1.4$ m³ of gas.

These requirements for gas must be injected during all or part of the associated periods, i.e.:
- during the time $t_1=4$ min, corresponding to the phase of rapid descent in the temperature of the vessel,
- during the time $t_f-t_1$ (7−4)=3 min, corresponding to the phase of slow descent in the temperature of the vessel, as far as its state of equilibrium close to 20° C.

The following associated flows of inert gas thus correspond to these gas volumes:
- for the first period $t_1=4$ min, the rapid drop in temperature step, the flow of nitrogen to be injected in order to compensate for the drop in temperature and to maintain the atmosphere inside the vessel is:

$Q_1=(V1_{gas}/t_1)\times 60=(32.4/4)\times 60=486$ Nm³/h of inert gas,

- for the second period $t_f-t_1$ (7−4)=3 min, the slow drop in temperature step, the flow of nitrogen to be injected in order to compensate for the drop in temperature and to maintain the atmosphere inside the vessel is:

$Q_2=(V2_{gas}/(t_f-t_1))\times 60=(1.4/3)\times 60=28$ Nm³/h of inert gas.

Details are given below of the conditions for practical illustrative embodiments, one according to the invention and the other provided for comparative purposes.

Test According to the Prior Art:

A sequence of aseptic washing steps is carried out with the aid of an aseptic solution at 80° C., and without taking any particular precautions, on the vessel evaluated above, having a volume of 75 m³, having previously been inerted, and of which the residual oxygen during the gaseous phase is in the order of 2.5%. This is followed immediately afterwards by a cold rinsing step, and the aspiration of air via the vent valves is observed, as expected. This aspiration involves a significant modification of the residual oxygen in the gaseous phase until, at the state of equilibrium at 20° C., the content of oxygen in the gaseous phase has passed from 2.5% to 13% in 7 minutes ($t_f$).

As will be clearly apparent to a person skilled in the art, the fact of having undertaken a pre-inerting of the vessel prior to washing makes it possible to better demonstrate the intake of air by the vessel due to thermal cycling.

Test with an Embodiment of the Method According to the Invention:

A sequence of aseptic washing steps is carried out once again with the aid of an aseptic solution at 80° C. on the same vessel, again having previously been inerted, and of which the residual oxygen during the gaseous phase at the end of the pre-inerting step is in the order of 3.5% (the difference in the residual oxygen compared to that of the preceding case is due solely to the experimental difficulty in this installation of obtaining an adjusted value to the nearest 1%). At the end of the hot aseptic washing step, and a few seconds (typically 5 seconds) before the start of the cold rinsing step, a flash injection of nitrogen is performed, depending on the predetermined requirement for inert gas indicated on the curves for the drops in the temperature of the vessel and for the water vapor pressure.

The calculated requirement (as previously explained above) reveals the need to inject 492 Nm³/h during the first 4 minutes of washing, followed by an injection of 24 Nm³/h during the following 3 minutes.

Technical constraints oblige us to inject a flow that is very slightly weaker than 465 Nm³/h.

The residual oxygen during the gaseous phase at the end of the rinsing step is 4.5%. However, the method has made it possible to preserve the atmosphere of the tank during this very rapid cooling step, with a consumption of gas very close to the stoichiometry.

An illustrative embodiment of the invention is described in detail above utilizing a calculation of the quantities of inert gas to be implemented in a differentiated fashion during the portion of the abrupt drop in the temperature of the vessel, and during the portion of the slow drop in the temperature of the vessel.

Figure 3:
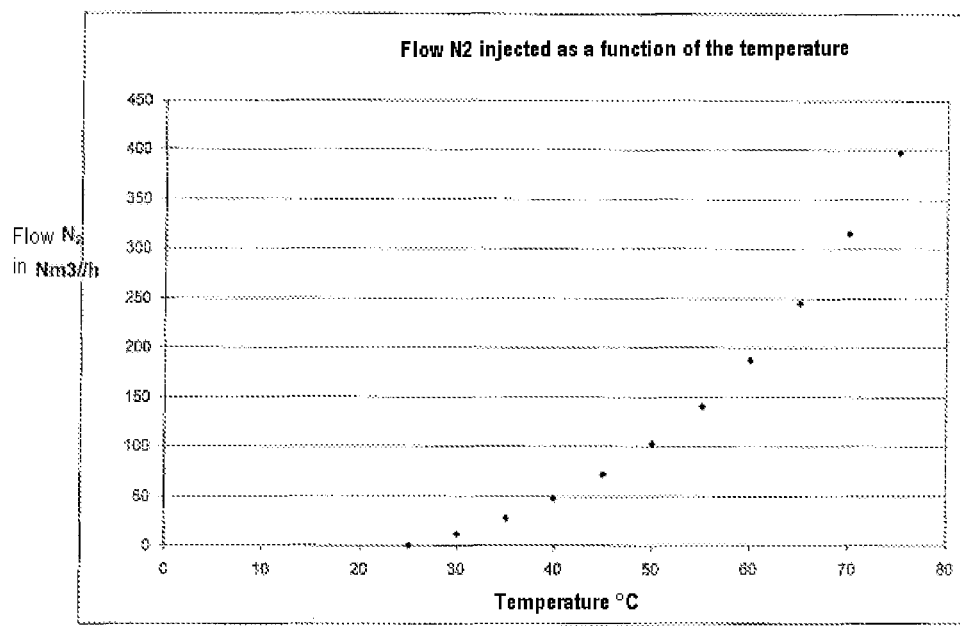
FIG. 3 depicts the flow curve for injected nitrogen depending on the temperature of the vessel, according to another of the embodiments of the invention.

Another embodiment of the invention, i.e. another method of calculating the requirement for inert gas and for regulating the injection of nitrogen, is described below with reference to FIG. 3, which is now presented.

This method utilizes the following approach, which is illustrated here one again in the case of the 75 m³ vessel utilized in the previous examples, which method enables the injected flow to be regulated with a proportional valve as a function of the temperature of the vessel:
- once again, the curve for the drop in temperature of the tank which occurs during this rinsing step (FIG. 1) has been established after the hot washing of the tank and during the rinsing step (i.e. during its traditional operation according to the prior art),
- consideration is also given to the water vapor pressure curve as a function of the temperature inside an enclosed space (FIG. 2, and the first two columns of the table below),
- each temperature of the vessel will be associated with a requirement for nitrogen (volume V in m³) which corresponds to the fact of suppressing the water vapor (as if the temperature of the vessel was 0° C. or −1° C.). This requirement (volume) of nitrogen is present in column 3 of the table.

If we now consider a numerical example, a vessel temperature of 70° C., the requirement for gas can be evaluated by the following equation:

$(P_{70}-P_0)\times 75$ m³$=(0.312-0.006)\times 75$ m³$=23$ m³

(This value can actually be found in column 3 opposite the temperature of 70° C.),
- let us consider, for example, the application of a flow for the period of 4 minutes in the portion of the curve exhibiting the abrupt drop in temperature, when column 4 of the table below gives the flow to be injected, opposite each temperature, based on this period of 4 minutes.

This flow thus corresponds to an application of the inerting until a water vapor pressure of zero is achieved.
- of course, as already mentioned, it is possible to consider stopping the inerting close to 25° C., in which case it is sufficient to subtract from each flow the given inerting flow for the temperature of 25° C., the result being column 5 in the following table, and the curve in the accompanying FIG. 3.
- of course, this is nothing more than an illustration of this embodiment of the invention utilizing only the time of 4 minutes corresponding to the abrupt drop in temperature, although this same approach could be utilized for a second time permitting the treatment of the second (slow) temperature gradient.

| °C. | Bar | Nitrogen requirement (m³) | Flow T = 4 min | Flow Stop at 25° C. |
|---|---|---|---|---|
| 100 | 1.013 | | | |
| 95 | 0.845 | | | |
| 90 | 0.701 | | | |
| 85 | 0.583 | | | |
| 80 | 0.474 | 36 | 533 | 297 |
| 75 | 0.385 | 29 | 433 | 397 |
| 70 | 0.312 | 23 | 351 | 315 |
| 65 | 0.25 | 19 | 281 | 245 |
| 60 | 0.199 | 15 | 224 | 188 |
| 55 | 0.157 | 12 | 177 | 141 |
| 50 | 0.123 | 9.2 | 138 | 102 |
| 45 | 0.096 | 7.2 | 108 | 72 |
| 40 | 0.074 | 5.6 | 83 | 47 |
| 35 | 0.056 | 4.2 | 63 | 27 |
| 30 | 0.042 | 3.2 | 47 | 11 |
| 25 | 0.032 | 2.4 | 36 | 0 |
| 20 | 0.023 | 1.7 | 26 | |
| 15 | 0.017 | 1.3 | 19 | |
| 10 | 0.012 | 0.9 | 14 | |
| 5 | 0.009 | 0.7 | 10 | |
| 0 | 0.006 | 0 | 7 | |

The use of an inerting gas, in this case nitrogen, has been illustrated in particular in the foregoing, although it can be readily appreciated that, depending on the contexts, the applications and the products in storage, it is possible to utilize other gases and mixtures of gases such as Ar, $CO_2$, He, etc., and their mixtures.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for treating tanks used for the storage and/or the preparation of products, the method comprising the steps of:
    washing the tank with a hot aseptic solution;
    rinsing the tank with cold water; and
    injecting an inert gas into the tank during all or part of the rinsing step to purge a volume of air present in the tank during the rinsing step, wherein the injection step includes the steps of:
        measuring a temperature decrease in the tank during the rinsing step;
        calculating a quantity of the inert gas required to be injected into the tank based on the measured temperature decrease in the tank during the rinsing step; and
        injecting the calculated quantity of the inert gas into the tank.

2. The method for treating tanks of claim 1, wherein the measurement step includes:
    a) measuring a curve for the decrease in the temperature of the tank, which occurs during the rinsing step; and
    b) deducing the said quantity of the inert gas required in order to perform the said treatment from the measured curve, based on the knowledge of the section of the curve exhibiting the most abrupt drop in temperature, and of the section of the curve corresponding to the slowest drop in temperature, which follows the curve exhibiting the most abrupt drop in temperature.

3. The method for treating tanks of claim 2, wherein the gas is injected during all or part of the section of the curve exhibiting the most abrupt drop in temperature, and in that the flow of inert gas to be injected is determined from the following formula:

$$Q_1 = (V1_{gas}/t_1) \times 60$$

(in $Nm^3/h$ of inert gas)
where:
$Q_1$ = the flow of inert gas to be injected during the section of the curve corresponding to the most abrupt drop in temperature
$V1_{gas} = (P_i - P_1) \times V_{vessel}$
$V_{vessel}$ = the volume of the vessel of the tank in $m^3$
$P_i$ = the water vapor saturation pressure at the temperature Ti of the vessel at the end of the washing step (in bar)
$P_1$ = the water vapor saturation pressure at the temperature $T_1$ of the vessel at the end of the section of the curve corresponding to the most abrupt drop in temperature (in bar)
$t_1$ = the duration of the section of the curve corresponding to the most abrupt drop in temperature.

4. The method for treating tanks of claim 2, wherein the gas is injected during all or part of the curve for the drop in the temperature of the tank which occurs during rinsing, and in that the flows of inert gas $Q_1$ and $Q_2$ to be injected are determined from the following formulae:

$$Q_1 = (V1_{gas}/t_i) \times 60$$

(in $Nm^3/h$ of inert gas)
where:
$Q_1$ = the flow of inert gas to be injected during the section of the curve corresponding to the most abrupt drop in temperature
$V1_{gas} = (P_i - P_1) \times V_{vessel}$
$V_{vessel}$ = the volume of the vessel of the tank in $m^3$
$P_i$ = the water vapor saturation pressure at the temperature Ti of the vessel at the end of the washing step (in bar)
$P_1$ = the water vapor saturation pressure at the temperature $T_1$ of the vessel at the end of the section of the curve corresponding to the most abrupt drop in temperature (in bar)
$t_1$ = the duration of the section of the curve corresponding to the most abrupt drop in temperature,
and:

$$Q_2 = (V2_{gas}/(t_f - t_1)) \times 60$$

(in $Nm^3/h$ of inert gas)
where:
$Q_2$ = the flow of inert gas to be injected during the section of the curve corresponding to the slowest drop in temperature, which follows the section of the curve exhibiting the most abrupt drop in temperature,
$V2_{gas} = (P_1 - P_2) \times V_{vessel}$
$V_{vessel}$ = the volume of the vessel in $m^3$
$P_1$ = the water vapor saturation pressure at the temperature $T_1$ of the vessel at the end of the section of the curve corresponding to the most abrupt drop in temperature (in bar)
$P_2$ = the water vapor saturation pressure at the temperature $T_f$ corresponding to the end of the section of the curve corresponding to the slowest drop in temperature (in bar)
$t_1$ = the duration of the section of the curve corresponding to the most abrupt drop in temperature
$t_f$ = the time taken, from the start of the rinsing step, to achieve the final equilibrium temperature.

5. The method for treating tanks of claim 1, wherein the injection commences before the start of the rinsing step.

6. The method for treating tanks of claim 5, wherein the inert gas is injected during the whole of the rinsing step.

7. The method for treating tanks of claim 5, wherein the injection of the inert gas is stopped when the temperature of the vessel has reached a given set point.

8. The method for treating tanks of claim 7, wherein the injection of the inert gas is stopped when the temperature of the vessel has reached 30° C., and preferably when it has reached 25° C.

9. The method for treating tanks of claim 5, wherein the injection of the inert gas is stopped when the temperature of the tank has reached the end of the section of the curve corresponding to the most abrupt drop in temperature.

10. The method for treating tanks of claim 1, wherein the injection commences after the start of the rinsing step.

11. The method for treating tanks of claim 10, wherein the inert gas is injected during the whole of the remaining rinsing step.

12. The method for treating tanks of claim 1, wherein a maintenance flow of the inert gas is maintained inside the tank after the injection of the inert gas is stopped, the said maintenance flow being lower than the flow of the inert gas injected during the injection step.

13. The method for treating tanks of claim 1, wherein the measurement step includes:
   a) measuring a curve for the decrease in the temperature of the tank, during the rinsing step;
   b) deducing knowledge of the section of the curve exhibiting the most abrupt drop in temperature, and of the section of the curve corresponding to the slowest drop in temperature, which follows the curve exhibiting the most abrupt drop in temperature, from the measured curve; and
   c) determining a requirement for the inert gas in order to perform the said treatment in the following manner:
      the requirement for the inert gas, expressed as a volume in $m^3$, corresponding to the fact of suppressing the water vapor associated with the temperature, is associated with each temperature;
      an injected flow of the inert gas, calculated for a treatment time t, is associated with each requirement thus expressed as a volume in $m^3$.

14. The method for treating tanks of claim 13, wherein the treatment time t is the duration of the section of the curve exhibiting the most abrupt drop in temperature.

15. The method for treating tanks of claim 13, wherein the injected flow is regulated with a proportional valve as a function of the temperature of the tank.

\* \* \* \* \*